United States Patent

Delignieres et al.

[11] Patent Number: 5,854,681
[45] Date of Patent: Dec. 29, 1998

[54] DEVICE AND METHOD MEASURING OPTICALLY THE CHARACTERISTICS OF A SUBSTANCE

[75] Inventors: Robert Delignieres, Mareil Marly; Christian Durand, Marly Le Roi, both of France

[73] Assignee: Institute Francais du Petrole, Reuil Malmaison, France

[21] Appl. No.: 809,447
[22] PCT Filed: Aug. 20, 1996
[86] PCT No.: PCT/FR96/01296
§ 371 Date: Jun. 30, 1997
§ 102(e) Date: Jun. 30, 1997
[87] PCT Pub. No.: WO97/07394
PCT Pub. Date: Feb. 27, 1997

[30] Foreign Application Priority Data

Aug. 21, 1995 [FR] France .................................. 95 10121
Nov. 30, 1995 [FR] France .................................. 95 14146

[51] Int. Cl.$^6$ ........................... G01N 21/25; G01N 21/00
[52] U.S. Cl. ......................... 386/416; 356/406; 356/432; 356/433

[58] Field of Search .................................. 356/406–408, 356/414, 416, 419–420, 425, 432–433

[56] References Cited

FOREIGN PATENT DOCUMENTS 2 701 318  8/1994  France.

Primary Examiner—Frank G. Font
Assistant Examiner—Amanda Merlino
Attorney, Agent, or Firm—Antonelli, Terry, Stout & Kraus, LLP

[57] ABSTRACT

According to an embodiment of the invention, the device comprises a unique optical path and a movable means providing for the selective passage of a light beam respectively through a transparent cell (4) containing a substance to be studied, at least one reference filter (6). The light reflected successively by one and the other of said two components is selectively applied to three filters (F 1–F3) which filter three wavelenghts selected as a function of the substance to be analyzed. Three detectors (D1–D3) are used to measure the successive light intensities which have gone through each of the filters, and from the measures obtained, it is possible to determine a correction coefficient before calculating a characteristic of the substance contained in the transparent cell.

21 Claims, 4 Drawing Sheets

DEVICE AND METHOD MEASURING OPTICALLY THE CHARACTERISTICS OF A SUBSTANCE

BACKGROUND OF THE INVENTION

1. Field of the Invention

The present invention relates to a device and to a method for measuring or detecting optically at least one characteristic or a variation of at least one characteristic of a reacting substance such as its absorbance for example, comprising notably of self-calibration of the device which overcomes possible drifts.

2. Description of the Prior Art

French Patent 701,318 describes a device for measuring optical characteristics of a reacting substance contained in a transparent cell such as its true absorbance. It comprises a light source, a first optical branch and a second optical branch, allowing selective passage of the light through the cell and outside it, an optical system for forming rays that have gone through the first or the second optical branch and a selective optical filter from an array of three selective filters, the first one being centred on a first wavelength corresponding to the isobestic point of the reacting substance, the second on a wavelength situated in a part of the light spectrum where the substance is the most sensitive and the third in another part of the spectrum where the substance is the least sensitive, means for measuring the intensity of the light that has gone through the optical system, and allowing determination of characteristics of the substance by combining intensity values of the light that has gone through the cell containing the substance and a reference cell.

This method used provides accurate and reliable results, but it does not overcome due notably to the aging of the various components and differences in the optical path or paths.

All the drift effects due notably to the aging and to the degradation of the various components of the device and to instabilities due to the optical paths are thus eliminated.

SUMMARY OF THE INVENTION

The object of the invention is to measure or to detect optically at least one characteristic of a reacting substance contained in a transparent cell, or the variations or changes in this substance, such as its true absorbance. The invention comprises at least one light source linked by at least one optical branch to a device allowing selective passage of the incident light coming from the light source through the cell and outside it, at least one reference filter, an optical system for forming rays that have gone through the device allowing selective passage and a selective optical filter, a device for measuring the intensity of the light that has gone through the optical system, a control unit, with the device allowing selective passage being controlled by said control unit and a power supply unit.

The device and the method according to the present invention improves the accuracy of measuring optical characteristics by performing a self-calibration of the device, for example, throughout the making of measurements.

The device for selecting the passage of the light is suited for allowing passage of the incident light through the cell and/or through at least one of the reference filters and/or directly outside the cell and at least one of the filters.

The optical filter can be selected from an array of three selective filters, the first one being centred on a first wavelength corresponding to the isobestic point of the reacting substance, the second on a wavelength in a part of the light spectrum where the substance is the most sensitive and the third in another part of the spectrum where the substance is the least sensitive.

The control unit comprises for example a control processor, a light intensity measuring signal acquisition unit and an interface unit for controlling the selection device.

According to an embodiment, the optical system comprises an optical derivation device for directing towards the three filters the light beams which have gone through the light passage selection device, the measuring device include three detectors for measuring the light that has gone through the three filters, and the electric switching device include elements for connecting intermittently device detectors with the control unit and a switch for connecting the light source, for example a lamp, to the power supply unit intermittently.

The reference cell and/or at least one of the reference filters are independently linked to the control unit.

The invention can also include a support common of the reference filter and the transparent cell, the common support being movable to rotate and/or to translate and the support being connected to the control unit.

According to an embodiment the invention comprises a first optical branch and a second optical branch allowing respectively passage of the incident light through the transparent cell and through at least one of the reference filters.

In order to improve the measuring accuracy, the device can include a device for measuring the ambient temperature and/or the temperature of the reacting substance, that can be connected to the control unit by the electric switching device and a device for measuring the supply voltage of the light source that can be connected to the control unit by the electric switching device.

The first branch and the second branch comprise each for example at least one optical filter.

The device for measuring the supply voltage of the light source can be connected to the control unit by the electric switching device.

The method according to the invention is characterized, according to an embodiment, which comprises automatic carrying out of measuring cycles under the control of a control unit, each one comprising:

a) a measuring stage where the light that has gone through the transparent cell is directed successively through three selective filters (F1, F2, F3) and the detected values of the light intensities coming from the three filters are acquired, b) a measuring stage where the light that has gone through at least a first reference medium is directed successively through the three filters and the detected values of the light intensities coming from the three filters are also acquired, c) a measuring stage where the light that has gone through at least a second reference medium is directed successively through the three filters and the detected values of the light intensities coming from the three filters are also acquired, and d) determining from the values measured in stages b) and c) for each of the filters a correction coefficient value Kcj relative to each of the filters and determining from the intensity values measured in stages a) and b) or a) and c) and from the correction coefficient associated with a filter characteristics of the reacting substance.

The reference media are for example reference filters having known transmittance values, or a neutral filter which does not modify much or any of the incident light.

Three selective filters are for example used, the first one being center on a first wavelength corresponding to the isobestic point of the reacting substance, the second on a wavelength in a part of the light spectrum where the substance is the most sensitive and the third in another part of the spectrum where the substance is the least sensitive.

The incident light can be passed through the air during stage b) or stage c).

According to another procedure, the incident light is respectively sent, during stages b) and c), through a first and through a second reference filter, the reference filters used in stages b) and c) having an associated transmittance value Te1, Te2, the difference Te1−Te2 being selected substantially equal to the maximum value of the transmittance of the substance contained in the cell.

BRIEF DESCRIPTION OF THE DRAWINGS

Other features and advantages of the device according to the invention and of the method for implementing it will be clear from reading the description hereafter of two embodiments given by way of non limitative examples, with reference to the accompanying drawings in which.

DESCRIPTION OF THE PREFERRED EMBODIMENTS

It is noted that the pH value of a solution is calculated by means of the relation as follows:

$$pH = pKi + \log x/(1-x) \quad (1),$$

where pKi is a constant and x is the basic fraction of the substance. This parameter x is connected to the absorbance A of the substance by the relation:

$$x = A/(c \cdot l \cdot \epsilon) \quad (2)$$

where c is the concentration, l the length of the optical path followed by the rays and $\epsilon$ the extinction coefficient of the cell. The absorbance is expressed as a function of the incident intensity Ii applied to the cell and of the intensity Ie coming therefrom by the relation:

$$A = \log(Ii/Ie) \quad (3).$$

The values of the absorbance A are subject to great fluctuations if only Ie is measured, because of the instability of the light source, for example a lamp. Indeed it is well-known that the characteristics of such a source vary with time. The color temperature is likely to vary owing to various causes linked with the lamp itself: progressive vaporization of the filament, aging of the casing, etc, and with the instability of the power supply. The result of all this is a notable change in the form of the frequency spectrum of the source. It can be observed for example that the color temperature of the source can decrease in time by more than 10%, which leads to great variations of the ratios between the light intensities applied to the various filters and consequently to wrong measurements.

Drifting may also be due to the optical path differences between the light source and the measuring system.

The transmittance value is simply deduced from the value of the absorbance A according to the relation: T=1-A.

Owing to its design and to its mode of implementation, the device and the method according to the invention precisely allow disregarding the effects due to the aging or to the degradation of the components in the device and/or possibly to instabilities or uncertainties due to the optical paths that may be different, by performing a self-calibration of the device for each wavelength, for example permanently.

Figure 1:
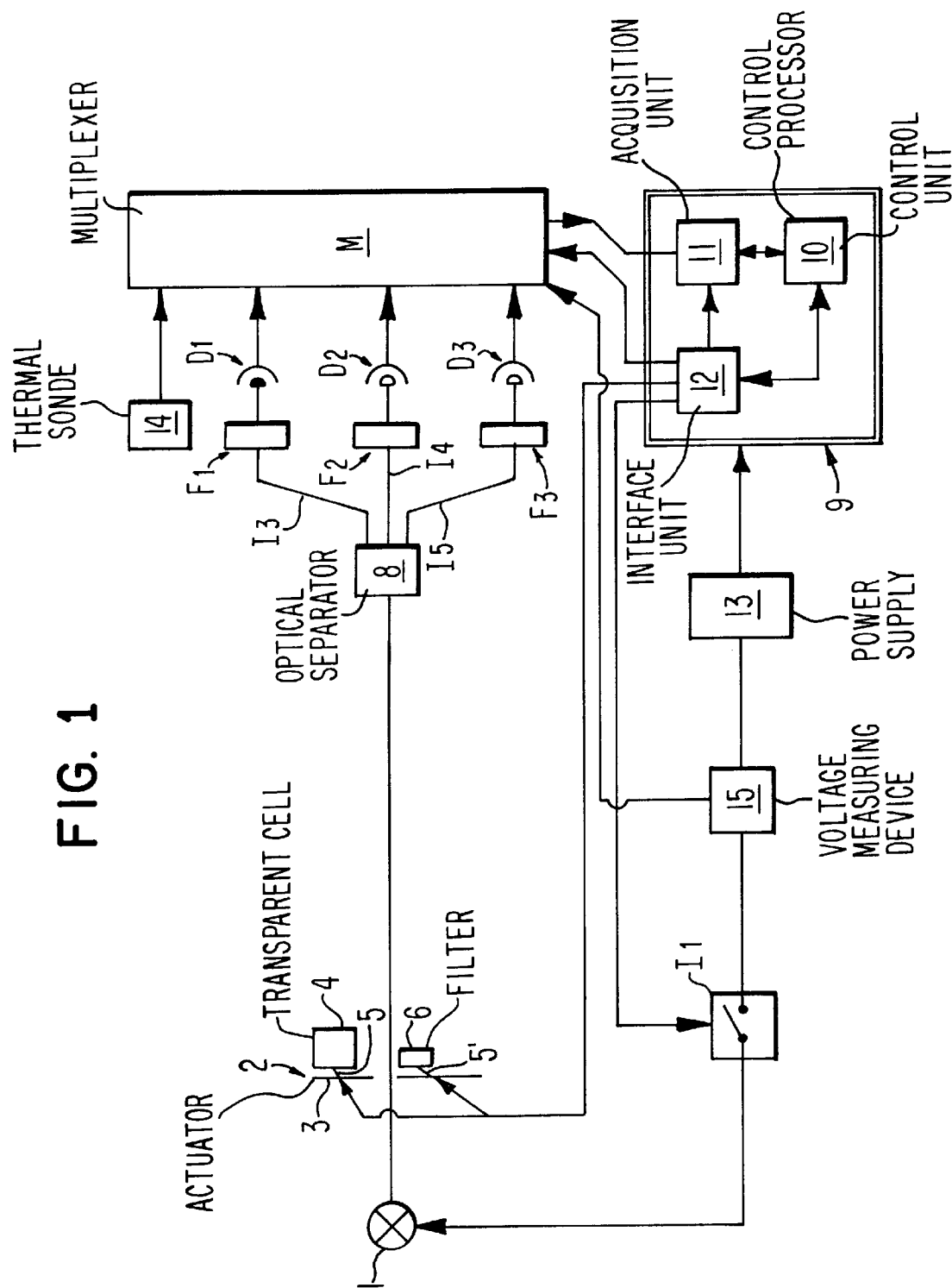
FIG. 1 diagrammatically shows a first embodiment of the device comprising a unique optical path and a movable device for selecting the passage of the incident light FIG. 2 diagrammatically shows a second embodiment comprising two optical paths for the passage of the incident light, FIGS. 3A and 3B diagrammatically show variants of the selection device according to the diagram of FIG. 1, and FIGS. 4 and 5 show in detail a flowchart example and a stage of acquisition of the measurements implementing the embodiment of FIG. 1.

According to a first embodiment described in FIG. 1, the device comprises a light source 1 such as a tungsten-filament halogen lamp. The light coming from source 1 is directed towards a movable assembly 2 allowing selective passage of the incident light. The assembly comprises for example a support 3 provided with a transparent cell 4 containing a reactive substance whose color variations are to be measured for example and connected to the support by an actuator 5, and with a reference such as a filter 6 itself connected to the support by an actuator 5'. The assembly 2 is movable to rotate and/or translate according to the structure thereof, so as to position the cell and/or the reference filter with respect to the beam of the incident light. The transparent cell 4 and the reference filter 6 are so arranged on support 3 that they allow the incident light to pass outside these two elements.

Figure 3A:
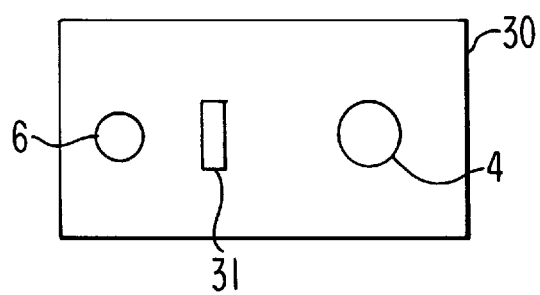
Figure 3B:
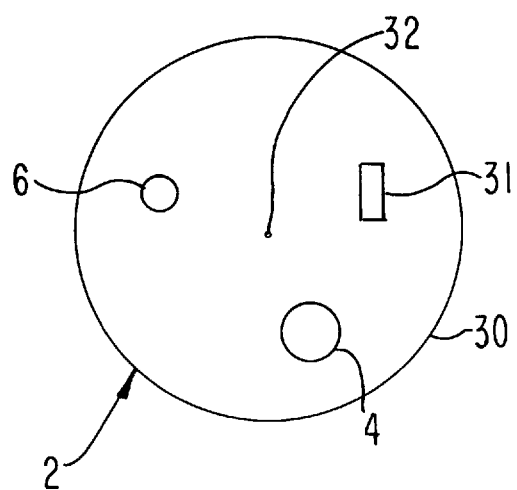

Various embodiment variants of the movable means are described in FIGS. 3A and 3B.

The light beam coming from cell 4, from reference filter 6 and/or that has passed outside these two elements is subdivided by an optical separator 8 into three beams that are directed by three optical fibers I3, I4, I5 respectively towards three coloured filters F1, F2, F3. These three filters allow respectively passage of the wavelengths L1=494 nm, L2=600 nm and L3=730 nm for example. The first wavelength L1 corresponds to the point referred to as the isobestic point of the colored substance where the absorbance of the basic fraction of the substance is equal to that of its acid fraction and therefore independent of the pH value. The second, L2, is the wavelength for which the coloured substance reacts most to the variations of the parameter to be measured. The third, L3, corresponds to a wavelength for which the absorbance of the coloured substance undergoes no variation. Each of the three filters F1, F2, F3 is for example coupled with a neutral filter whose transmittance is selected so as to balance the light intensities that go through the three branches I3, I4, I5. The light that has gone respectively through the three colored filters F1, F2, F3 is applied to three photo-electric detectors D1, D2, D3. The signals they deliver are applied to three inputs of a processing device M, a multiplexer for example.

Without departing from the scope of the invention, the signals delivered by the photo-electric detectors can also be acquired and processed directly according to processes known to persons skilled in the art.

The device is managed by a control unit 9 including a control processor 10, an acquisition unit 11 connected to the output of multiplexer M and an interface unit 12 for controlling the various components of the device and multiplexer M. The device also comprises a power supply unit 13 such as an electric accumulator in case of autonomous working of the device, this power supply unit being connected to lamp 1 by means of a switch I1 also controlled by interface unit 12. The device also preferably includes a thermal sonde 14 placed in the vicinity of the elements of the device for measuring the ambient temperature and/or the temperature of the reactive substance, this sonde being connected to an input of multiplexer M, as well as a voltmeter for measuring the voltage delivered by power supply unit 13.

Interface unit 12 is connected for example individually to the transparent cell and to the reference filter which, in the embodiment example of FIG. 1, are separate elements, in order to control, by acting on actuators 5 and 5' for example, the positioning thereof with respect to the incident light beam.

According to other embodiments, interface unit 12 controls the movable support for positioning the elements with respect to the light beam.

The transparent cell being directly or indirectly movable, it can be linked with an optional external source containing reactive products by means of flexible pipes.

The measuring method applied allows disregarding the degradation of the components by determining a correction coefficient for each wavelength of the filters, preferably permanently.

Figure 4:
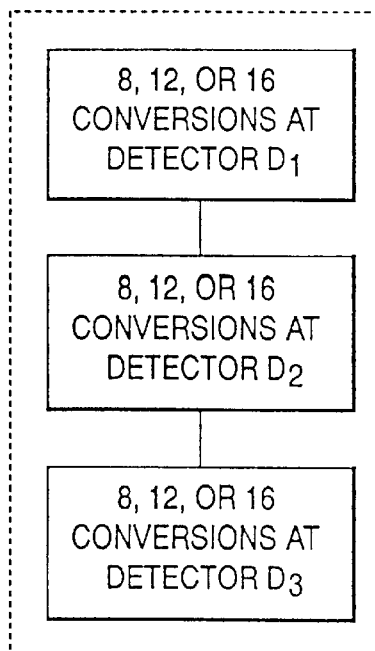
Figure 5:
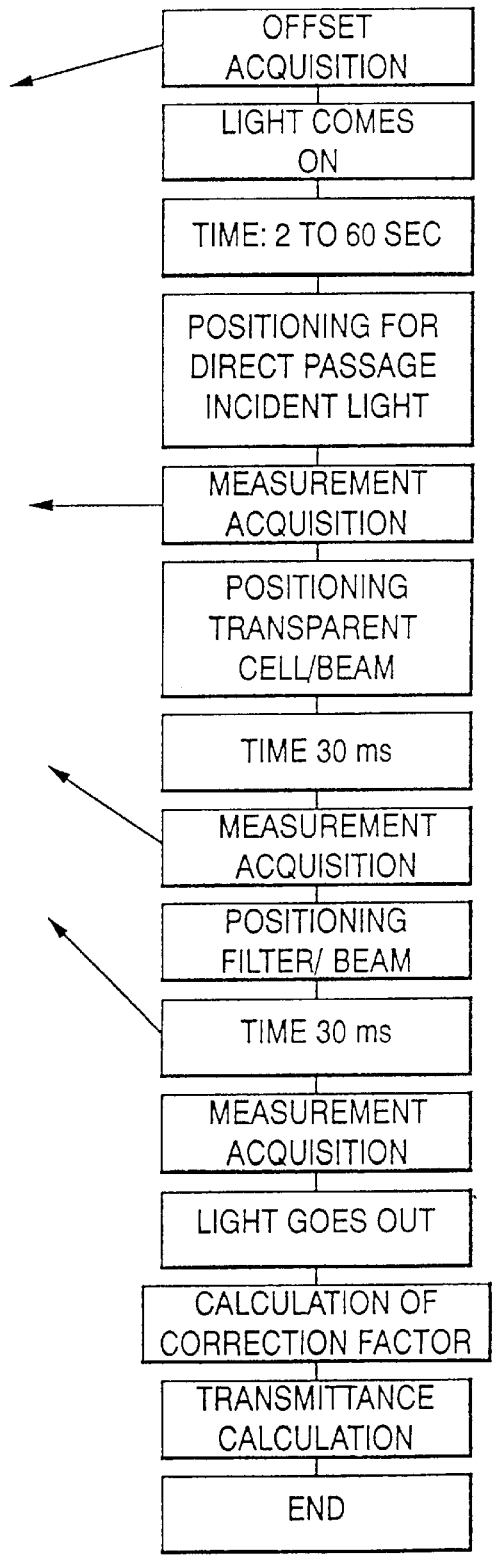

As can be seen in the flowchart of FIGS. 4 and 5, each measuring cycle first comprises a series of 8, 12 or 16 measurements referred to as "offset" measurements, where the noise signals affecting detectors D1, D2, D3 are measured sequentially by a sequential control of multiplexer M, these signals being acquired and digitized by acquisition unit 11. Once the noise signals have been measured, the lamp is turned on by opening switch I1, then the cell and the reference filter are positioned so as to allow direct passage of the incident light towards filters F1, F2, F3, and a first sequence of measuring the light that has gone directly through the transparent cell and successively filtered through filters F1, F2, F3 is performed. The transparent cell is thereafter positioned so that the incident light goes through it and a second series of measuring the light that has gone through the transparent cell and successively filtered through filters F1, F2, F3 is performed in the form of an analogous sequence. Then, by acting for example on actuators 5 and 5', the transparent cell is repositioned in its initial position and the reference filter is arranged so as to allow passage of the incident light therethrough, and a third sequence of measuring the light that has gone through the reference filter and successively filtered through filters F1, F2, F3 is performed in the form of an analogous sequence.

At the end of this measuring cycle for each wavelength a value has been obtained associated with one of the filters F1, F2 or F3 and bearing subscript j in the description hereafter, a measurement of the incident light $Mij$, a value of the light $Msj$ that has gone through the transparent cell containing the substance likely to vary and the value of the light that has gone through the reference filter $Mrj$.

For each wavelength proper to a filter, the value of the transmittance of the reference filter is determined according to the formula:

$$Trj = (Krj \ 19 \ Mrj)/Mij$$

where Kr is the coupling coefficient of the reference filter.

Knowing the value of the initial transmittance for the reference filter, Te, the correction coefficient associated with a wavelength value bearing subscript j is obtained:

$$Kcj = (Te/Trj).$$

Then, from this correction coefficient, the value of the transmittance of the substance contained in the transparent cell is determined for a wavelength value:

$$Tsj = Kcj \cdot [(Ksj \cdot Msj)/Mij]$$

where Ksj is the coupling coefficient of the cell.

The absorbance value of the substance contained in the transparent cell is then directly deduced for each wavelength from the expression as follows:

$$Asj = 1 - Tsj.$$

The absorbances As1, As2 and As3 corresponding to the three wavelengths of the coloured filters F1–F3 are thus calculated. Applying relation (2) allows to showing that the value of the basic fraction x of the substance studied is obtained by the relation as follows:

$$x = k \cdot (As2 - As3)/(As1 - As3)$$

where k is a constant, and that owing to the comparative method used, any degradation of all the components of the device for each wavelength can be totally disregarded. Control processor 10 can determine for example the pH value of the analyzed substance therefrom.

In order to complete the previous measurements, an acquisition of the temperature measured by thermal sonde 14 and of the voltage applied to lamp 1 measured by element 15 is preferably performed, and these values are taken into account so as to correct errors. Indeed it has been observed that the measuring errors are of the order of 4% when the temperature increases from 20° C. to 60° C. In order to compensate for these variations, central processor 10 applies to the measurements a correction as a function of the temperature variation, such as a linear correction for example.

In order to minimize measuring errors even further, it is also possible to take account of the voltage variations (due to the discharge of the accumulator in case of an autonomous power supply) which have the effect of varying the light intensity of lamp 1. Taking account of these temperature and voltage variations allows the obtaining of measurements accurate to within 1%.

Figure 2:
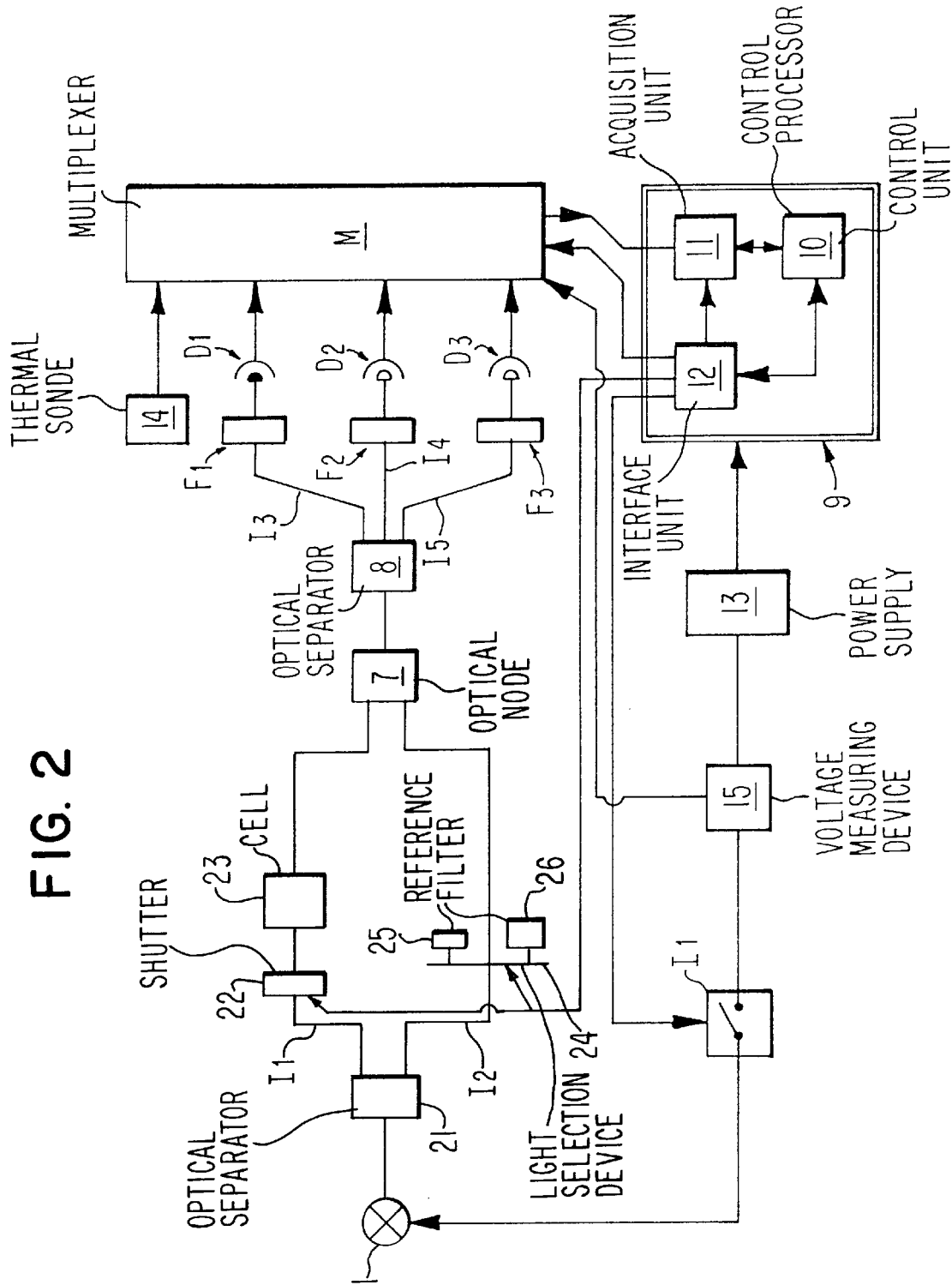

FIG. 2 describes another embodiment comprising two optical paths instead of the unique optical path of FIG. 1 and two reference filters.

The light coming from source 1 is subdivided by an optical separator 21 into two light beams that are directed by of optical fibers 11, 12 for example, the first one towards a main optical branch comprising a shutter 22 and a cell 23 containing the reactive substance whose color variations are to be measured, the second towards a derived optical branch for forming a beam passing outside cell 23 and through a unit 24 including two reference filters 25 and 26 having respectively initial transmittance values Te1 and Te2. Shutter 22 and light passage selection device 24 are connected to interface unit 12 which controls their opening or positioning with respect to the incident light beam so as to allow selective passage of the beams, according to a sequence substantially identical to that described in connection with FIG. 1, through respectively the two reference filters and the transparent cell.

Reference filters 25 and 26 have transmittance values so selected that the difference Te1–Te2 is substantially of the same order as the minimum possible transmittance of the substance to be measured contained in the cell. This advantageously allows calibration of this measurement, irrespective of the amount of light that has gone through the medium.

The two optical branches are connected to an optical node 7 which allows transmission of the light beam coming selectively from one or the other branch towards an optical separator 8. The latter subdivides the beam into three beams directed towards the three filters as described in FIG. 1.

The measuring method is carried out according to a sequence analogous to that described in connection with FIG. 1, the light being sent respectively through each of the reference filters and through the transparent cell.

At the end of this measuring cycle for each wavelength a value has been obtained associated with one of the filters F1, F2 or F3 and bearing subscript j hereafter, a value of the light Msj that has gone through the transparent cell containing the substance likely to vary and values of the light that has gone through the two reference filters 25 and 26, Mfj and Mfj, bearing subscripts f and f.

The correction coefficient is calculated for example as follows:

For each wavelength bearing subscript j, the transmittance value of the substance is determined to the two reference filters 25 and 26, which correspond to the ratio between the light measurement after it has gone through the transparent cell containing the substance and the light going through a reference filter, corrected by the transfer coefficient of the filter:
we get:
for filter $f(25), Tsj=(Msj)/(Kcj \cdot Kfj \cdot Mfj)$, and
for filter $f(26), T'sj=(Msj)/(Kcj \cdot Kfj \cdot Mfj)$
where Kfj and Kfs are the known transfer values of the filters f and f for the wavelength j.
Kcj is the correction factor or calibration factor of the device that is sought.

The transmittance difference for a wavelength j is known by calibration performed for example before implementing the process according to the invention.

Thus, for each wavelength, the transmittance difference Δj relative to the two filters bearing subscripts f and f is determined:

$$\Delta j = Tsj - T'sj = (Msj)/(Kcj)[1/(Kfj \cdot Mfj) - 1/(Kfj \cdot Mfj)]$$

The value of the correction factor Kcj for a wavelength bearing subscript j is deduced from this equation:

$$Kcj = (Msj)/\Delta j)[1/(Kfj \cdot Mfj) - 1/(Kfj \cdot Mfj)].$$

The transmittance value of the substance contained in the transparent cell is determined from this correction coefficient.

One of the reference filters can of course be a neutral filter leading to no or little change with regard to the incident light.

FIG. 3A describes an embodiment example for the light translating passage selection device.

It comprises, arranged on a common support 30, the transparent cell 4, a reference filter 6 and for example a slot 31 allowing direct passage of the light.

The slot can of course be replaced by a second reference filter as described with reference to FIG. 2.

Support 30 translates for example with the aid of well-known devices, such as a stepping motor or any other available prime move known to the person skilled in the art allowing it to be shifted, and preferably simultaneously an indexing of the elements present on the support so as to position them precisely with respect to the incident light beam in order to carry out the stages of the method.

FIG. 3B shows a device 2 mounted for example on a fulcrum pin 32.

Similarly, fulcrum pin 32 is connected to a control device such as a motor (not shown in the FIG. 3B) connected to unit 12, for example, that controls it so as to position the cell and the reference filter or filters according to the sequences performed in the course of the method.

The slots, filters and supports can of course have any shape and they are selected as a function of the spacing requirement and of the characteristics of the light beam.

We claim:

1. A device for measuring and/or for detecting optically at least one characteristic or a variation of at least one characteristic of a reacting substance contained in a transparent cell, comprising at least one light source connected by at least one optical branch to at least one device controlling selective passage of incident light through the transparent cell, at least one reference filter, an optical system for forming light beams which have passed through the at least one device for controlling selective passage and a selective optical filter including an array of three selective filters, the first filter passing a wavelength corresponding to an isobestic point of the reacting substance, the second filter passing a wavelength in a part of the light spectrum where the reacting substance is most sensitive and the third filter passing a wavelength in another part of the spectrum where the reacting substance is least sensitive, a device for measuring an intensity of the light passing through the optical system, a control unit and a power supply unit, and wherein the control unit determines transmittance of the at least one reference filter which is determined for each of the wavelengths in accordance with the relationship $Trj=(Kr \cdot Mrj)/Mij$ with Kr being a coupling coefficient of the at least one reference filter, Mrj being a measurement of incident light passing through the at least one reference filter for each wavelength j and being MIJ being a measurement of incident light to the selective optical filter, determines for the j wavelengths a value of a correction coefficient $Kcj=Te/Trj$ where Te is an initial transmittance for the at least one reference filter, determines for the correction coefficient Kcj a value of the transmittance of a substance contained in the transparent cell $Tsj = Kcj[(Ks \cdot Msj)/Mij]$ where Ks is a coupling coefficient of the transparent cell and determines a value of absorbance of As/Asj of the reacting substance contained in the transparent cell where $Asj=1-Tsj$.

2. A device as claimed in claim 1, wherein the control unit includes a control processor, an acquisition unit for acquiring signals of the measured light intensity and an interface unit for controlling the at least one device controlling selective passage.

3. A device as claimed in claim .1, wherein the optical system comprises a device for directing light towards the three selective filters which have passed through the at least one device controlling selective passage, the device for measuring comprises three detectors for measuring light which has passed through the three selective filters, and a multiplexer connecting the three detectors to the control unit for connecting intermittently the detectors with the control unit and a switch for intermittently connecting the light source to the power supply unit.

4. A device as claimed in claim 2, wherein the optical system comprises a device for directing light towards the three selective filters which have passed through the at least one device, for controlling selective passage the device for measuring intensity comprises three detectors for measuring light which has passed through the three selective filters, and a multiplexer connecting the three detectors to the control unit for connecting intermittently the three detectors with the control unit and a switch for intermittently connecting the at least one light source to the power supply unit.

5. A device as claimed in claim 1, wherein one of the at least one reference filter is connected independently to the control unit.

6. A device as claimed in claim 1, wherein the at least one device controlling selective passage comprises a support common to the at least one reference filter and the transparent cell and the common support is movable to rotate and/or to translate the support and the support is connected to the control unit.

7. A device as claimed in claim 1, comprising a first optical branch and a second optical branch providing respectively passage of the incident light through the transparent cell and through the at least one reference filter.

8. A device as claimed in claim 2, comprising a first optical branch and a second optical branch providing respectively passage of the incident light through the transparent cell and through the at least one reference filter.

9. A device as claimed in claim comprising a first optical branch and a second optical branch providing respectively passage of the incident light through the transparent cell and through the at least one reference filter.

10. A device as claimed in claim 3, further comprising a measurement device for measuring ambient temperature and/or temperature of the reacting substance and which is connected to the control unit by a multiplexer.

11. A device as claimed in claim 1, further comprising a voltage measuring device for measuring a supply voltage of the at least one light source which is connected to the control unit by an electric switch.

12. A device as claimed in claim 2, wherein the at least one device controlling selective passage comprises a support common to the at least one reference filter and transparent cell, the common support is movable to rotate and/or to translate the support and the support is connected to the control unit.

13. A device as claimed in claim 3, wherein the at least one device controlling selective passage comprises a support common to the at least one reference filter and transparent cell, the common support is movable to rotate and/or to translate the support and the support is connected to the control unit.

14. A device as claimed in claim 4, wherein the at least one device controlling selective passage comprises a support common to the at least one reference filter and transparent cell, the common support is movable to rotate and/or to translate the support and the support is connected to the control unit.

15. A device as claimed in claim 5, wherein the at least one device controlling selective passage comprises a support common to the at least one reference filter and transparent cell, the common support is movable to rotate and/or to translate the support and the support is connected to the control unit.

16. A device as claimed in claim 2, wherein one of the at least one reference filter is connected independently to the control unit.

17. A device as claimed in claim 3, wherein one of the at least one reference filter is connected independently to the control unit.

18. A device as claimed in claim 15, wherein one of the at least one reference filter is connected independently to the control unit.

19. A method for detecting and/or for measuring optically changes in a reacting substance contained in a transparent cell, with measuring cycles carried out under control of a control unit, comprising:

(a) directing light that has passed through the transparent cell successively through three selective filters and acquiring values $Msj$ of light intensities coming from the three filters;

(b) directing light that has passed through a first reference medium successively through the three selective filters and acquiring values $Mrj$ of light intensities coming from the three selective filters;

(c) directing light that has passed through a second reference medium successively through the three selective filters and acquiring detected values $Mrj$ of the light intensities coming from the three selective filters; and (d) determining from values measured in steps (b) and (c) for each of the selective filters a correction coefficient value $Kcj$ relative to each of the selective filters, and determining from intensity values measured in steps (a) and (b) or (a) and (c) and from correction coefficient associated with a filter characteristic of the reacting substance, and wherein transmittance of the at least one reference filter is determined for each of the wavelengths in accordance with the relationship $Trj = (Kr \cdot Mrj)/Mij$ with $Kr$ being a coupling coefficient of the at least one reference filter, $Mrj$ is a measurement of incident light passing through the at least one reference filter for each wavelength $j$ and $Mij$ being a measurement of incident light to the three selective filters, for the $j$ wavelengths a value is determined of a correction coefficient $Kcj = Te/Trj$ where $Te$ is an initial transmittance for the at least one reference filter, for the correction coefficient $Kcj$ a value is determined of the transmittance of the reacting substance contained in the cell where $Tsj = Kcj[(Ks \cdot Msj)/Mij]$ where $Ks$ is a coupling coefficient of the cell and a value of absorbance is determined of $As/Asj$ of the reacting substance contained in the transparent cell where $Asj = 1 - Tsj$.

20. A method as claimed in claim 19 wherein the incident light is passed directly through air during step (b) or step (c).

21. A method as claimed in claim 19, wherein during step (b) and step (c) incident light is directed respectively through a first and a second reference filter, each of the reference filters having an associated transmittance value $Te1$, $Te2$, and the difference $Te1-Te2$ is substantially equal to the minimum transmittance value of the reacting substance contained in the transparent cell.

* * * * *